US012668237B2

(12) United States Patent
Takahashi et al.

(10) Patent No.: US 12,668,237 B2
(45) Date of Patent: Jun. 30, 2026

(54) VEHICLE CONTROL DEVICE, VEHICLE CONTROL METHOD, AND STORAGE MEDIUM STORING A VEHICLE CONTROL PROGRAM

(71) Applicant: YAZAKI CORPORATION, Tokyo (JP)

(72) Inventors: Yoshihiro Takahashi, Susono (JP); Jungang Guan, Susono (JP); Yuki Takahashi, Susono (JP)

(73) Assignee: YAZAKI CORPORATION, Tokyo (JP)

( * ) Notice: Subject to any disclaimer, the term of this patent is extended or adjusted under 35 U.S.C. 154(b) by 45 days.

(21) Appl. No.: 18/908,737

(22) Filed: Oct. 7, 2024

(65) Prior Publication Data

US 2025/0128703 A1     Apr. 24, 2025

(30) Foreign Application Priority Data

Oct. 19, 2023     (JP) ................................. 2023-180029

(51) Int. Cl.
*B60W 30/09*     (2012.01)
*A61B 5/11*     (2006.01)
(Continued)

(52) U.S. Cl.
CPC ........... *B60W 30/09* (2013.01); *A61B 5/1116* (2013.01); *B60W 30/12* (2013.01);
(Continued)

(58) Field of Classification Search
CPC .... B60W 30/09; B60W 30/12; B60W 30/146; B60W 50/14; B60W 2540/221; B60W 2540/30; B60W 2420/403; B60W 2540/10; B60W 2540/12; B60W 2540/18; B60W 2540/223; B60W 2720/10; B60W 2040/0818; B60W 2040/0827; B60W 2040/0836; B60W 2040/0845; B60W 2040/0863; B60W 2040/0872; B60W 40/09; B60W 40/10; B60W 40/105; B60W 40/107; B60W 40/109; B60W 2540/225; B60W 2540/227; B60W 2540/229; B60W 2540/24; B60W 2540/26; A61B 5/1116;
(Continued)

(56) References Cited

U.S. PATENT DOCUMENTS

2019/0129416 A1*  5/2019  Upmanue ............ G05D 1/0061
2020/0148214 A1*  5/2020  Tamagaki ............... B60R 21/00
(Continued)

FOREIGN PATENT DOCUMENTS

JP          2021-14232 A     2/2021
JP          2022-128656 A     9/2022

*Primary Examiner* — Esvinder Singh
(74) *Attorney, Agent, or Firm* — KENEALY VAIDYA LLP

(57) ABSTRACT

A vehicle control device includes a detection unit that detects a motion of a driver of a vehicle, a behavior of the vehicle, and biological information of the driver, an abnormal sign determination unit that determines whether there is an abnormal sign on the driver based on the motion of the driver, the behavior of the vehicle, and the biological information of the driver, and a vehicle controller that performs different types of vehicle control according to a situation of the abnormal sign on the driver.

9 Claims, 8 Drawing Sheets

(51) Int. Cl.
    *B60W 30/12*         (2020.01)
    *B60W 30/14*         (2006.01)
    *B60W 50/14*         (2020.01)

(52) U.S. Cl.
    CPC .......... *B60W 30/146* (2013.01); *B60W 50/14*
        (2013.01); *A61B 2503/22* (2013.01); *B60W*
        *2540/221* (2020.02); *B60W 2540/30* (2013.01)

(58) Field of Classification Search
    CPC . A61B 2503/22; G05D 1/0055; G05D 1/0066
    See application file for complete search history.

(56)             References Cited

U.S. PATENT DOCUMENTS

| 2021/0001866 A1* | 1/2021 | Yoshimura ............ G06F 18/256 |
|---|---|---|
| 2021/0016783 A1 | 1/2021 | Watanabe et al. |
| 2021/0362729 A1 | 11/2021 | Watanabe et al. |
| 2022/0032923 A1* | 2/2022 | Park ......................... A61B 5/18 |
| 2024/0324926 A1* | 10/2024 | Yoshida ................. A61B 5/746 |
| 2025/0033612 A1* | 1/2025 | Ito ......................... B60W 50/14 |

\* cited by examiner

FIG.2

| ABNORMAL SIGN STATE | | | |
|---|---|---|---|
| DRIVER'S MOTION | BIOLOGICAL INFORMATION | VEHICLE BEHAVIOR | DRIVER'S POSTURE |
| 1 | 1 | 0 | 0 |
| 0 | 1 | 1 | 0 |
| 1 | 0 | 1 | 0 |
| 1 | 0 | 0 | 0 |
| 0 | 1 | 0 | 0 |
| 0 | 0 | 1 | 0 |

FIG.3

| FUNCTION/MOTION CONDITION | ROAD EXCLUSIVE FOR AUTOMOBILES | | | GENERAL ROAD | | |
|---|---|---|---|---|---|---|
| | NORMAL | DURING CONSTRUCTION OR THE LIKE | BAD WEATHER | NORMAL | DURING CONSTRUCTION OR THE LIKE | BAD WEATHER |
| MAXIMUM SPEED SUPPRESSION | O | O | O | O | O | O |
| ERRONEOUS PEDAL OPERATION REDUCTION | O | O | O | O | O | O |
| FRONT COLLISION WARNING | O | O | O | O | O | O |
| COLLISION REDUCTION BRAKE | O | O | O | O | O | O |
| COLLISION AVOIDANCE | O | - | - | O | - | - |
| LANE DEVIATION WARNING LDW | O | - | - | O | - | - |
| LANE DEVIATION SUPPRESSION LDA, LKAS | O | - | - | O | - | - |
| EVACUATION/STOPPING | O | - | - | O | - | - |
| FOLLOW-UP TRAVELING | O | - | - | - | - | - |

CONTROL WITHOUT OPERATION RESTRICTION (MAXIMUM SPEED SUPPRESSION – COLLISION REDUCTION BRAKE)

CONTROL WITH OPERATION RESTRICTION (COLLISION AVOIDANCE – LANE DEVIATION SUPPRESSION LDA, LKAS)

CONTROL USABLE ONLY ON SPECIFIC ROAD (EVACUATION/STOPPING – FOLLOW-UP TRAVELING)

VEHICLE CONTROL DEVICE, VEHICLE CONTROL METHOD, AND STORAGE MEDIUM STORING A VEHICLE CONTROL PROGRAM

CROSS-REFERENCE TO RELATED APPLICATION(S)

The present application claims priority to and incorporates by reference the entire contents of Japanese Patent Application No. 2023-180029 filed in Japan on Oct. 19, 2023.

BACKGROUND OF THE INVENTION

1. Field of the Invention

The present invention relates to a vehicle control device, a vehicle control method, and a storage medium storing a vehicle control program.

2. Description of the Related Art

Conventionally, as related to a vehicle control device, a vehicle control method, and a vehicle control program, for example, as described in Japanese Patent Application Laid-open No. 2021-14232, a device that performs vehicle control such as driving assistance when abnormality of a driver of a vehicle is detected is known. This device performs vehicle control according to a traveling scene of a vehicle.

The above-described device has room for improvement in that it is difficult to sufficiently secure safety of the vehicle travel when the driver is abnormal. Therefore, it is desirable to perform vehicle control such as driving assistance at an early stage when an abnormal sign is detected on the driver.

SUMMARY OF THE INVENTION

Therefore, an object of the present invention is to provide a vehicle control device, a vehicle control method, and a vehicle control program capable of achieving safety of vehicle travel with respect to abnormality of a driver.

In order to achieve the above mentioned object, a vehicle control device according to one aspect of the present invention includes a detection unit that is configured to detect a motion of a driver of a vehicle, a behavior of the vehicle, and biological information of the driver; an abnormal sign determination unit that is configured to determine whether there is an abnormal sign on the driver based on the motion of the driver, the behavior of the vehicle, and the biological information of the driver; and a vehicle controller that is configured to perform different types of vehicle control according to a situation of the abnormal sign on the driver.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2 is a diagram illustrating a relationship between an abnormal sign state of a driver and abnormal sign detection;

FIG. 3 is a diagram illustrating a relationship between driving assistance control and operation restriction in the vehicle control device according to the embodiment;

DETAILED DESCRIPTION OF THE PREFERRED EMBODIMENTS

Hereinafter, an embodiment according to the present invention will be described in detail with reference to the drawings. Note that the present invention is not limited by this embodiment. In addition, constituent elements in the following embodiment include those that can be easily replaced by those skilled in the art or those that are substantially the same.

EMBODIMENT

Figure 1:
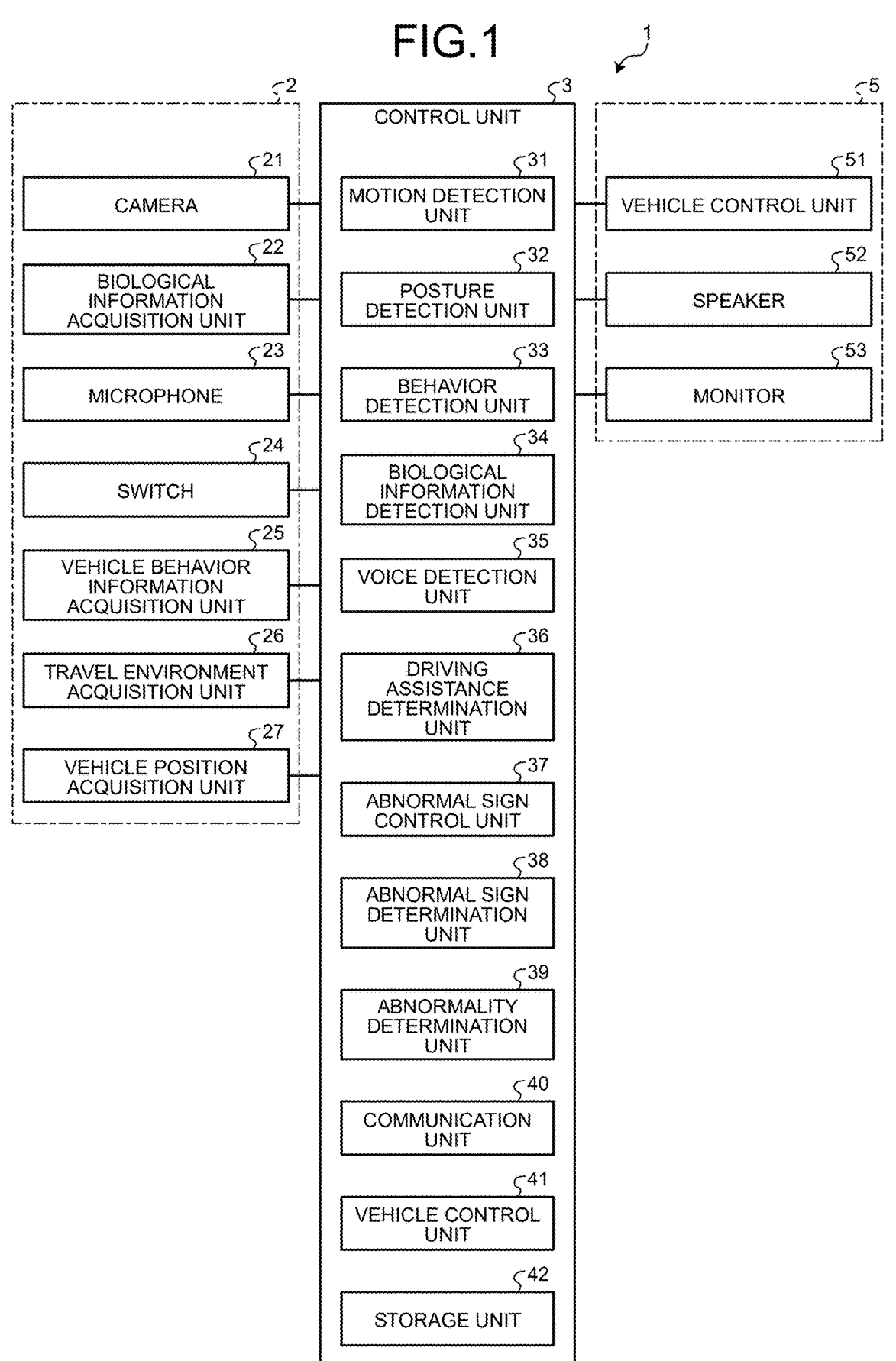
FIG. 1 is a block diagram illustrating an outline of an electrical configuration of a vehicle control device according to an embodiment.

The present embodiment relates to a vehicle control device, a vehicle control method, and a vehicle control program. As illustrated in FIG. 1, a vehicle control device 1 is a device that detects an abnormal sign and an abnormal state of a driver of a vehicle and performs vehicle control to handle them. Here, the abnormal state is a state in which the driver cannot perform normal driving, and is, for example, an incapacity to drive state. The sign of abnormality is a state different from the normal state of the driver before the abnormal state.

The vehicle control device 1 includes an input unit 2, a controller 3, and an output unit 5. The input unit 2 inputs information or data related to abnormal sign detection, abnormality detection, vehicle control, and the like of the driver to the controller 3. The input unit 2 includes, for example, a camera 21, a biological information acquisition unit 22, a microphone 23, a switch 24, a vehicle behavior information acquisition unit 25, a travel environment acquisition unit 26, and a vehicle position acquisition unit 27.

The camera 21 is an imaging unit that images the driver, and is installed in the vehicle and inputs an image of the driver to the controller 3. The camera 21 functions as a motion acquisition unit that acquires motion information of the driver. The camera 21 is provided, for example, to be able to image the driver from the front in the vehicle. Furthermore, the camera 21 may individually include an imaging unit that images an upper body of the driver and an imaging unit that images a face of the driver.

The biological information acquisition unit 22 acquires biological information of the driver, and corresponds to, for example, a heart rate measuring instrument that measures a heart rate and a pulse rate, a sphygmomanometer that measures blood pressure, a thermometer that measures a body temperature, and the like. As the heart rate measuring instrument, the sphygmomanometer, and the thermometer, for example, a wearable device that can be mounted on the driver and measured is used. Furthermore, as the heart rate measuring instrument, for example, a millimeter wave radar may be used. In a case where the millimeter wave radar is used as the heart rate measuring instrument, the heart rate can be measured without contact with the driver, and the respiratory rate can also be measured. The biological information acquisition unit 22 can communicate with the controller 3 in a wired or wireless manner, and inputs biological information of the driver to the controller 3.

The microphone 23 detects a driver's voice, generates and acquires voice information, and inputs the voice information to the controller 3. Further, the microphone 23 acquires voice information or response information of a response of the driver to a call from the vehicle control device 1. The switch 24 includes, for example, a push button, and acquires response information of the driver to a call from the vehicle control device 1. The switch 24 inputs response information to the controller 3. Note that the input unit 2 may include devices, sensors, or the like other than the camera 21, the biological information acquisition unit 22, the microphone 23, the switch 24, and the vehicle behavior information acquisition unit 25 described above as long as the input unit 2 can acquire information for detecting the abnormal state or the abnormal sign on the driver.

The vehicle behavior information acquisition unit 25 is a device that acquires vehicle behavior information, and corresponds to, for example, a vehicle speed sensor, a steering angle sensor, a camera, and a millimeter wave radar. The vehicle speed sensor detects a traveling speed of the vehicle. The steering angle sensor detects a steering wheel steering angle of the vehicle and provides determination information of unsteadiness of vehicle travel. For example, the camera captures an image of the front of the vehicle, and provides determination information on whether the vehicle has deviated from a lane, determination information on whether the vehicle has exceeded a stop line, and inter-vehicle distance information with a preceding vehicle. The millimeter wave radar detects a distance to the preceding vehicle or an obstacle in front of the vehicle. The vehicle behavior information acquisition unit 25 may include all or some of the vehicle speed sensor, the steering angle sensor, the camera, and the millimeter-wave radar, or may include a device, a sensor, or the like other than the vehicle speed sensor, the steering angle sensor, the camera, and the millimeter wave radar described above as long as information for detecting the abnormal behavior of the vehicle can be acquired.

The travel environment acquisition unit 26 is a device that acquires travel environment information of the vehicle, and acquires, for example, the travel environment information such as the weather at the device position of the vehicle, the situation of the travel path of the vehicle, and whether there is a stop space on the travel path. The travel environment acquisition unit 26 corresponds to, for example, a rainfall sensor, a camera that images the outside of the vehicle, or the like. In addition, the travel environment acquisition unit 26 may acquire weather information through communication with the outside of the vehicle and acquire stop space information on the travel path.

The vehicle position acquisition unit 27 is a device that acquires traveling position information of the vehicle, and corresponds to, for example, a navigation system.

The output unit 5 is a device that operates based on a signal output from the controller 3, and corresponds to, for example, a vehicle control unit 51, a speaker 52, and a monitor 53. The vehicle control unit 51 includes a control device that performs braking control, driving control, and steering control of the vehicle in response to a control signal output from the controller 3. For example, the vehicle control unit 51 includes, for example, individual control devices that perform the braking control, driving control, and steering control of the vehicle. The speaker 52 calls the driver by voice based on the signal output from the controller 3. The speaker 52 functions as a notification unit that gives a notification to the driver through hearing, and operates and outputs a voice in response to a voice signal from the controller 3, for example. The monitor 53 functions as a notification unit that visually notifies the driver, and for example, a liquid crystal display or the like is used and operates in response to a display signal from the controller 3. In addition, the monitor 53 may be used not only as a display device but also as an input device by using a touch panel or the like.

The controller 3 is a controller that performs vehicle control of the driver, and includes, for example, a computer. The controller 3 includes a central processing unit (CPU), a read only memory (ROM), a random access memory (RAM), and the like. For example, the controller 3 loads a vehicle control program stored in the ROM into the RAM, and executes the vehicle control program by the CPU, thereby performing vehicle control.

The controller 3 includes a motion detection unit 31, a posture detection unit 32, a behavior detection unit 33, a biological information detection unit 34, a voice detection unit 35, a driving assistance determination unit 36, an abnormal sign controller 37, an abnormal sign determination unit 38, an abnormality determination unit 39, a vehicle controller 41, a communication unit 40, and a storage unit 42. The motion detection unit 31, the posture detection unit 32, the behavior detection unit 33, the biological information detection unit 34, the voice detection unit 35, the driving assistance determination unit 36, the abnormal sign controller 37, the abnormal sign determination unit 38, the abnormality determination unit 39, and the vehicle controller 41 are configured by, for example, introducing a vehicle control program into the controller 3. In addition, the motion detection unit 31, the posture detection unit 32, the behavior detection unit 33, the biological information detection unit 34, the voice detection unit 35, the driving assistance determination unit 36, the abnormal sign controller 37, the abnormal sign determination unit 38, the abnormality determination unit 39, and the vehicle controller 41 may be configured as individual controllers.

The motion detection unit 31 detects the motion of the driver, and detects the motion of the driver using an image analysis method or an image recognition method based on image information output from the camera 21. As the image analysis method and the image recognition method, known image analysis methods and image recognition methods may be used. The motion detection unit 31 detects a posture, a motion, an expression, and the like of the driver. For example, the motion detection unit 31 detects a motion in an abnormal state of the driver and a motion that is an abnormal sign on the driver. In addition, the motion detection unit 31 detects a motion related to a disease of the driver.

The motion that becomes the abnormal sign on the driver corresponds to, for example, a painful motion when the driver feels a pain in the body of the driver. The painful motion includes a motion and an expression of the driver feeling pain, and corresponds to, for example, a motion of pressing a chest, a motion of pressing a head, a motion of pressing a back, a motion of pressing a shoulder, a motion of pressing a neck, and a painful expression. The painful motion of the driver is a motion of an abnormal sign before the driver becomes unable to drive. When the motion detection unit 31 detects the painful motion, the vehicle control device 1 can detect that the driver is in an abnormal state at an early stage. Furthermore, by including a motion of pressing the chest, a motion of pressing the head, and a motion of pressing the back as the painful motion, the motion detection unit 31 can detect an abnormal sign of a heart disease, a brain disease, and an arterial disease (aortic aneurysm, aortic dissection). It is said that accidents caused by heart disease, brain disease, and arterial disease account for 70% or more of accidents caused by driver's diseases. Therefore, by detecting an abnormal sign of a heart disease, a brain disease, and an arterial disease, it is possible to accurately improve the safety of vehicle travel.

The posture detection unit 32 detects the posture of the driver, and detects the posture of the driver using an image analysis method or an image recognition method based on image information output from the camera 21. The posture detection unit 32 detects an abnormal sign on the driver and a posture to be in an abnormal state. The posture of the driver in the abnormal state corresponds to, for example, unsafe posture of the driver. The unsafe posture is a state in which a posture is unsafe from a normal driving posture, and corresponds to, for example, a state in which a steering wheel is not firmly held by a seat, a state in which a driver is crouched, and the like.

The behavior detection unit 33 detects a behavior of the vehicle, and detects an abnormal behavior of the vehicle based on the behavior information acquired by the vehicle behavior information acquisition unit 25. For example, the behavior detection unit 33 detects the abnormal behavior of the vehicle caused by the abnormal sign on the driver. Specifically, the behavior detection unit 33 detects, as the abnormal behavior of the vehicle, lane deviation of the vehicle, unsteady traveling of the vehicle, operation delay of the vehicle, exceeding a stop line, traveling with a risk of a front collision, and the like. Therefore, the behavior detection unit 33 functions as a behavior detection unit of the vehicle.

The biological information detection unit 34 detects biological information of the driver, and detects biological information that is an abnormal sign on the driver based on the biological information of the driver acquired by the biological information acquisition unit 22. For example, the biological information detection unit 34 detects all or some of an increase in the pulse rate by a predetermined value or more, a decrease in the pulse rate by a predetermined value or less, an increase in the blood pressure by a predetermined value or more, a decrease in the blood pressure by a predetermined value or less, a pulse wave abnormality, an arrhythmia, an increase in the respiratory rate by a predetermined number or more, and a decrease in the respiratory rate by a predetermined number or less.

The voice detection unit 35 detects the voice of the driver, and detects voice information that is the abnormal sign on the driver based on the voice information acquired by the microphone 23. For example, the voice detection unit 35 detects a voice related to a disease of the driver and detects a voice that is an abnormal sign on the driver. For example, the voice detection unit 35 detects a groaning sound and a cry of the driver as a sound that is the abnormal sign on the driver. In this case, the voice detection unit 35 functions as a motion detection unit that detects the motion of the driver.

The driving assistance determination unit 36 determines whether execution of the driving assistance control is restricted based on the travel environment of the vehicle or the like. For example, in a case where a plurality of driving assistance controls is possible as the driving assistance control of the vehicle, there is a case where a part of the control cannot be executed according to the travel environment. The driving assistance determination unit 36 determines whether execution of driving assistance control is restricted based on the travel environment information acquired by the travel environment acquisition unit 26, and determines which driving assistance control is restricted from being executed.

For example, as illustrated in FIG. 3, when the travel environment is good (normal case) as the driving assistance control of the vehicle, in a case where maximum speed suppression control, erroneous pedal operation reduction control, front collision warning control, collision reduction brake control, the collision avoidance control, the lane deviation warning control, the lane deviation suppression control, evacuation/stopping control, and follow-up traveling control can be executed, some control may not be executed according to the travel environment. For example, there is a case where lane detection cannot be performed when a travel path of a vehicle is under construction or there is bad weather, and execution of the collision avoidance control, the lane deviation warning control, the lane deviation suppression control, and the evacuation/stopping control is restricted. When the vehicle is not traveling on a road exclusive for automobiles, the execution of the follow-up traveling control may be restricted. In this manner, the driving assistance determination unit 36 determines which driving assistance control is restricted to be executed based on the travel environment of the vehicle or the like. Even when the driver is in an abnormal sign state or an abnormal state and the driving assistance control is restricted, the vehicle control device 1 achieves safety of vehicle travel by other driving assistance control or vehicle control.

The abnormal sign controller 37 performs abnormal sign response control when the driver has an abnormal sign. For example, the abnormal sign controller 37 performs a call step to ask the driver whether driving is possible, and determines whether there is a response from the driver. In this case, the abnormal sign controller 37 outputs a control signal to the speaker 52 or the monitor 53 to issue a notification by voice output or image display, and inputs a response signal from the driver through the microphone 23 or the switch 24. When the driving assistance control is restricted, the abnormal sign controller 37 notifies the driver of the restriction. In this case, the abnormal sign controller 37 outputs a control signal to the speaker 52 or the monitor 53 to issue a notification by voice output or image display.

The abnormal sign determination unit 38 determines whether there is an abnormal sign on the driver. For example, the abnormal sign determination unit 38 determines whether there is the abnormal sign on the driver based on detection results of the motion detection unit 31, the behavior detection unit 33, and the biological information detection unit 34.

For example, as illustrated in FIG. 2, the abnormal sign determination unit 38 determines that the driver is in the abnormal sign state when a part of the motion detection unit 31, the behavior detection unit 33, and the biological information detection unit 34 detects that there is the abnormal sign on the driver. That is, in a case where at least one of the motion that is the abnormal sign on the driver by the motion detection unit 31, the abnormal behavior of the vehicle by the behavior detection unit 33, and the biological information that is an abnormal sign by the biological information detection unit 34 is detected, the abnormal sign determination unit 38 determines that the driver is in the abnormal sign state. Meanwhile, in a case where none of the motion that is the abnormal sign on the driver by the motion detection unit 31, the abnormal behavior of the vehicle by the behavior detection unit 33, and the biological information that is the abnormal sign by the biological information detection unit 34 is detected, the abnormal sign determination unit 38 determines that the driver is not in the abnormal sign state. In addition, in a case where all of the motion that is the abnormal sign on the driver by the motion detection unit 31, the abnormal behavior of the vehicle by the behavior detection unit 33, and the biological information that is the abnormal sign by the biological information detection unit 34 are detected, the abnormal sign determination unit 38 determines that the driver is not in the abnormal sign state. In this case, the abnormality determination unit 39 determines that the driver is in the abnormal state.

The abnormality determination unit 39 determines whether the driver is in the abnormal state. For example, when a closed eye state, a syncope state, or a white of eye state of the driver is detected by the motion detection unit 31, the abnormality determination unit 39 determines that the driver is in an incapacity to drive state and in the abnormal state. When the unsafe posture state of the driver is detected by the posture detection unit 32, the abnormality determination unit 39 determines that the driver is in the abnormal state. In addition, even when the driver is not in the closed eye state, the syncope state, the white of the eye state, or the unsafe posture state, the abnormality determination unit 39 may determine that the driver is in the abnormal state when the driver is in the incapacity to drive state.

In addition, the abnormality determination unit 39 determines that the driver is in an abnormal state in a case where all of the motion that is the abnormal sign on the driver by the motion detection unit 31, the abnormal behavior of the vehicle by the behavior detection unit 33, and the biological information that is the abnormal sign by the biological information detection unit 34 are detected. The abnormality determination unit 39 determines that the driver is in the abnormal state when the abnormal sign determination unit 38 determines that there is the abnormal sign and when the driver does not respond to a call as to whether the driver can drive through the speaker 52 or the monitor 53.

The communication unit 40 is a part that performs wireless communication with the outside of the controller 3. For example, the communication unit 40 performs wireless communication with the biological information acquisition unit 22 to acquire the biological information of the driver.

When the abnormality determination unit 39 determines that the driver is in the abnormal state or when the abnormal sign determination unit 38 determines that the driver is in the abnormal sign state, the vehicle controller 41 outputs a control signal to the vehicle control unit 51, and executes driving assistance control and vehicle control to achieve safety of vehicle travel.

The storage unit 42 stores information, data, or the like regarding vehicle control. For example, the storage unit 42 stores a vehicle control program, control data, and the like.

Next, an operation of the vehicle control device 1, a vehicle control method, and a vehicle control program according to the present embodiment will be described.

Figure 4:
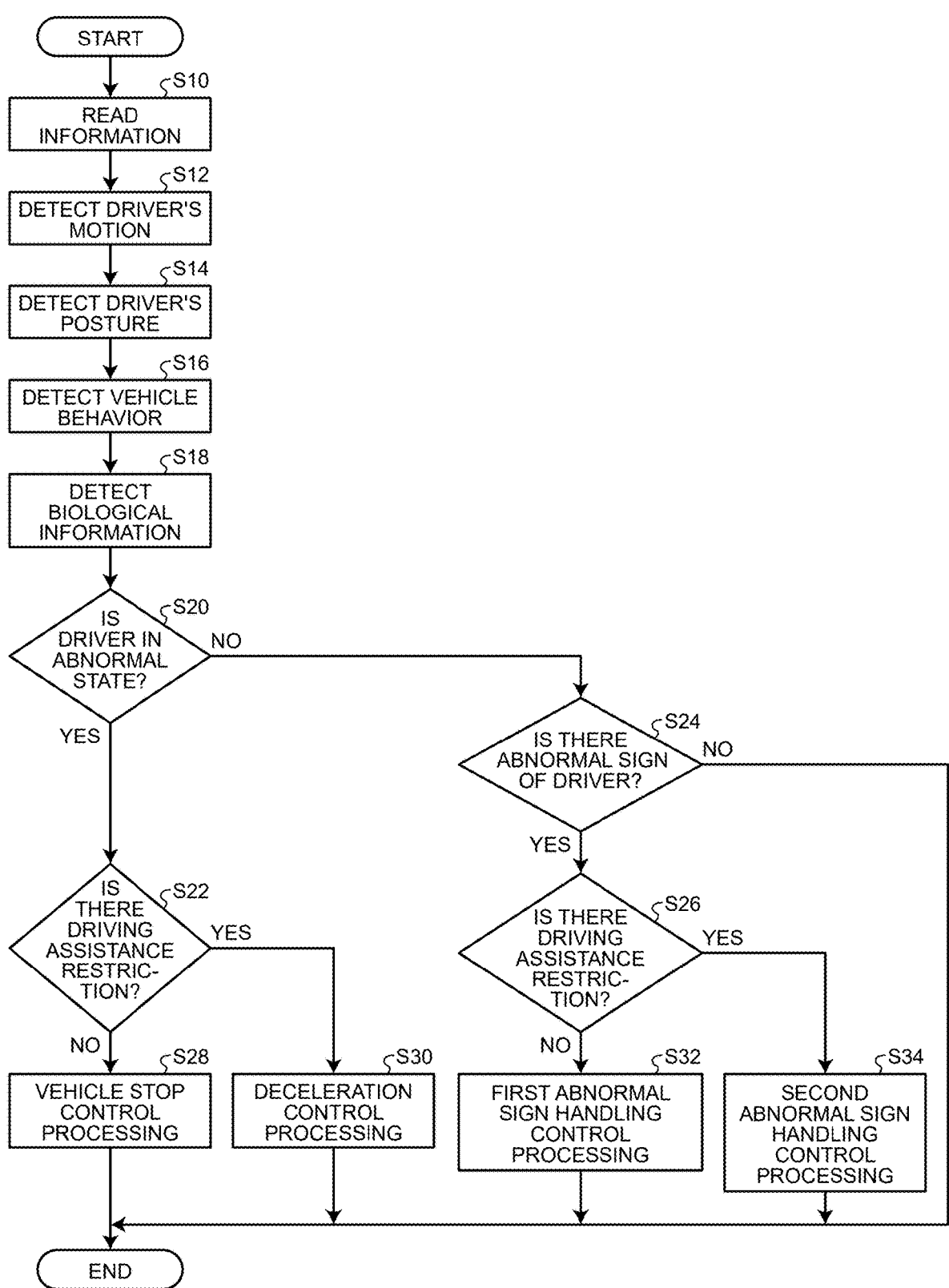
FIG. 4 is a flowchart illustrating an operation of the vehicle control device, a vehicle control method, and a vehicle control program according to the embodiment.

FIG. 4 is a flowchart illustrating an operation of the vehicle control device 1, the vehicle control method, and the vehicle control program. A series of control processing in the flowchart of FIG. 4 is started by, for example, turning on the ignition of the vehicle or turning on the power switch of the vehicle, and is repeatedly executed at a predetermined cycle by the controller 3.

First, Step S10 in FIG. 4 (hereinafter, simply referred to as "S10", and the same applies to steps after S10), a step of reading information related to vehicle control is performed. As the information regarding the vehicle control, for example, information output from the camera 21, the biological information acquisition unit 22, the microphone 23, the switch 24, the vehicle behavior information acquisition unit 25, the travel environment acquisition unit 26, and the vehicle position acquisition unit 27 is input to and read by the controller 3.

Then, the step proceeds to S12, and a motion detection step of a driver is performed. The motion detection step is a step of detecting the motion of the driver, and is performed by the motion detection unit 31 using, for example, an image analysis method or an image recognition method based on image information output from the camera 21. The motion detection unit 31 detects, as a motion in an abnormal state of the driver, a state in which the steering wheel is released, syncope, eye closure, white of eye, and the like. In addition, the motion detection unit 31 detects a painful motion in a case where the driver feels a pain in the body of the driver as a motion that is the abnormal sign on the driver. Specifically, the motion detection unit 31 detects, as the painful motion, a motion of pressing the chest, a motion of pressing the head, a motion of pressing the back, a motion of pressing the shoulder, a motion of pressing the neck, and a painful expression. In the motion detection step, an abnormal sign due to a disease can be detected by detecting a painful motion of the driver. Therefore, the vehicle control device 1, the vehicle control method, and the vehicle control program can accurately detect abnormality of the driver at an early stage.

The motion detection step may be performed by the voice detection unit 35 using a voice analysis method or the like based on the voice information output from the microphone 23. The voice detection unit 35 detects a voice related to a disease of the driver and detects a voice that is an abnormal sign on the driver. For example, the voice detection unit 35 detects a groaning sound and a cry of the driver as a sound that is the abnormal sign on the driver.

Then, the step proceeds to S14, and the posture detection step of the driver is performed. The posture detection step is a step of detecting the posture of the driver, and is performed by the posture detection unit 32 using, for example, an image analysis method or an image recognition method based on image information output from the camera 21. The posture detection unit 32 detects an unsafe posture state or the like as the motion in the abnormal state of the driver.

Then, the step proceeds to S16, and a vehicle behavior detection step is performed. The vehicle behavior detection step is a step of detecting the behavior of the vehicle, and is performed by the behavior detection unit 33 based on the behavior information acquired by the vehicle behavior information acquisition unit 25. For example, the behavior detection unit 33 detects the abnormal behavior of the vehicle caused by the abnormal sign on the driver. Specifically, the behavior detection unit 33 detects, as the abnormal behavior of the vehicle, lane deviation of the vehicle, unsteady traveling of the vehicle, operation delay of the vehicle, exceeding a stop line, traveling with a risk of a front collision, and the like.

Then, the step proceeds to S18, and a biological information detection step is performed. The biological information detection step is a step of detecting biological information of the driver, and is performed by the biological information detection unit 34. The biological information detection unit 34 detects biological information that is the abnormal sign on the driver. For example, the biological information detection unit 34 detects all or some of an increase in the pulse rate by a predetermined value or more, a decrease in the pulse rate by a predetermined value or less, an increase in the blood pressure by a predetermined value or more, a decrease in the blood pressure by a predetermined value or less, a pulse wave abnormality, an arrhythmia, an increase in the respiratory rate by a predetermined number or more, and a decrease in the respiratory rate by a predetermined number or less.

Then, the step proceeds to S20, and it is determined whether the driver is in the abnormal state. This step is performed, for example, by the abnormality determination unit 39. The abnormality determination unit 39 determines whether the driver is in the abnormal state based on the detection results of the motion detection unit 31, the posture detection unit 32, the behavior detection unit 33, and the biological information detection unit 34. For example, when the abnormal state such as unsafe posture of the driver is detected by the posture detection unit 32 and the abnormal state is continuously detected for a preset time T1, the abnormality determination unit 39 determines that the driver is in the abnormal state. For example, the time T1 is set to a time between 5 seconds and 10 seconds. As described above, the vehicle control device 1 can suppress erroneous determination of the abnormal state by determining that the driver is in the abnormal state when the driver is in the abnormal state continuously during the time T1.

In addition, the abnormality determination unit 39 determines that the driver is in the abnormal state when all of the motion detection unit 31, the behavior detection unit 33, and the biological information detection unit 34 detect that the driver is in the abnormal sign state and the abnormal sign state is continuously detected for a preset time T2. For example, the time T2 is set to be longer than the time T1, and is set to be a time between 10 to 60 seconds. As described above, the vehicle control device 1 can suppress the erroneous determination of the abnormal state by determining that the driver is in the abnormal state when the driver is continuously in the abnormal sign state during the time T2.

Meanwhile, the abnormality determination unit 39 determines that the driver is not in the abnormal state in a case where the abnormal state is not continuously detected for the time T1 by the posture detection unit 32 and the abnormal sign state is not continuously detected for the time T2 by all of the motion detection unit 31, the behavior detection unit 33, and the biological information detection unit 34.

When it is determined in S20 that the driver is in the abnormal state, it is determined whether there is a restriction on the execution of the driving assistance control (S22). This determination step is executed by the driving assistance determination unit 36. For example, the driving assistance determination unit 36 determines whether the execution of the driving assistance control is restricted based on the traveling environment information acquired by the travel environment acquisition unit 26, and determines which driving assistance control is restricted from being executed. Specifically, the driving assistance determination unit 36 determines whether execution of the collision avoidance control, the lane deviation warning control, the lane deviation suppression control, and the evacuation/stopping control among the maximum speed suppression control, the erroneous pedal operation reduction control, the front collision warning control, the collision reduction brake control, the collision avoidance control, the lane deviation warning control, the lane deviation suppression control, the evacuation/stopping control, and the follow-up traveling control is restricted.

When it is determined that the execution of the driving assistance control is not restricted in S22, vehicle stop control processing is executed (S28). Details of the vehicle stop control processing will be described later. Meanwhile, when it is determined in S22 that the execution of the driving assistance control is restricted, deceleration control processing is executed (S30). Details of the deceleration control processing will be described later. When the vehicle stop control processing of S28 and the deceleration control processing of S30 are ended, the series of control processing of FIG. 4 is ended.

When it is determined that the driver is not in the abnormal state in S20, it is determined whether the driver is in the abnormal sign state (S24). This step is performed by the abnormal sign determination unit 38, for example. The abnormal sign determination unit 38 determines whether the driver is in the abnormal sign state based on the detection results of the motion detection unit 31, the behavior detection unit 33, and the biological information detection unit 34. For example, in a case where some of the motion detection unit 31, the behavior detection unit 33, and the biological information detection unit 34 detect that the driver is in the abnormal sign state and the abnormal sign state is continuously detected for a preset time T3, the abnormal sign determination unit 38 determines that the driver is in the abnormal sign state. For example, the time T3 is set to be shorter than the time T2 and is set to be a time between 10 to 30 seconds. As described above, the vehicle control device 1 can suppress erroneous determination of the abnormal sign state by determining that the driver is in the abnormal sign state when the driver is continuously in the abnormal sign state during the time T3.

Meanwhile, when the abnormal sign state is not continuously detected for the time T3 by some of the motion detection unit 31, the behavior detection unit 33, and the biological information detection unit 34, the abnormal sign determination unit 38 determines that the driver is not in the abnormal sign state.

When it is determined that the driver is not in the abnormal sign state in S24, the series of control processing in FIG. 4 ends. Meanwhile, when it is determined in S24 that the driver is in the abnormal sign state, it is determined whether there is a restriction on the execution of the driving assistance control (S26). This determination step is executed by the driving assistance determination unit 36. For example, the driving assistance determination unit 36 determines whether the execution of the driving assistance control is restricted based on the traveling environment information acquired by the travel environment acquisition unit 26, and determines which driving assistance control is restricted from being executed. Specifically, the driving assistance determination unit 36 determines whether execution of the collision avoidance control, the lane deviation warning control, the lane deviation suppression control, and the evacuation/stopping control among the maximum speed suppression control, the erroneous pedal operation reduction control, the front collision warning control, the collision reduction brake control, the collision avoidance control, the lane deviation warning control, the lane deviation suppression control, the evacuation/stopping control, and the follow-up traveling control is restricted.

When it is determined that the execution of the driving assistance control is not restricted in S26, first abnormal sign handling control processing is executed (S32). Details of the first abnormal sign handling control processing will be described later. Meanwhile, when it is determined in S26 that the execution of the driving assistance control is restricted, second abnormal sign handling control processing is executed (S34). Details of the second abnormal sign handling control processing will be described later. When the first abnormal sign handling control processing in S32 and the second abnormal sign handling control processing in S34 are ended, the series of control processing in FIG. 4 is ended.

Figure 5:
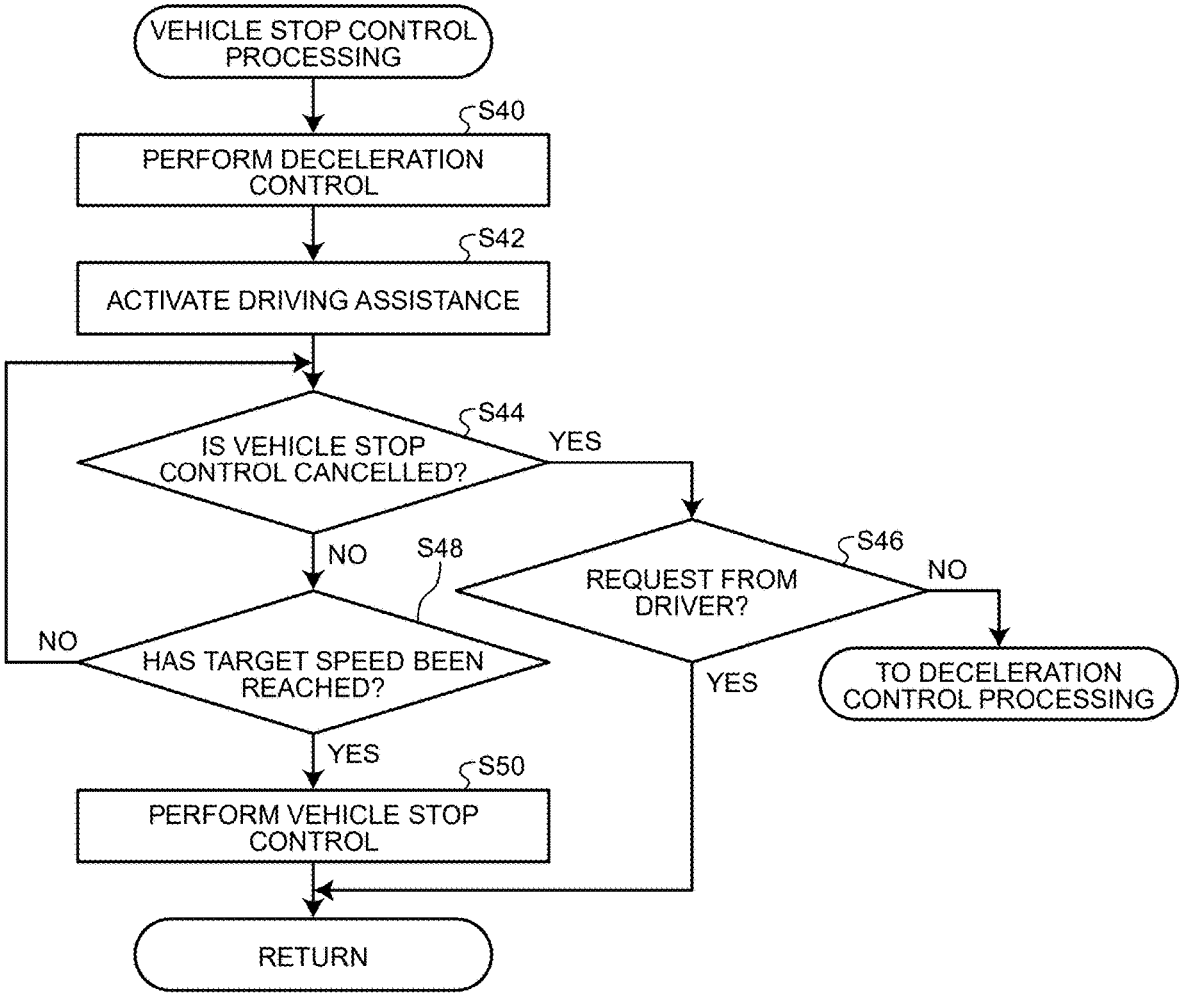
FIG. 5 is a flowchart illustrating the operation of the vehicle control device, the vehicle control method, and vehicle stop control processing in the vehicle control program according to the embodiment.

FIG. 5 is a flowchart of vehicle stop control processing illustrated in S28 of FIG. 4. The control processing of the flowchart of FIG. 5 is executed by the controller 3, for example.

First, as illustrated in S40 of FIG. 5, a deceleration control step is performed. The deceleration control step is processing of decelerating the vehicle by automatic control, and is executed, for example, by gradually decelerating the vehicle until the target speed reaches at deceleration approximately equal to the deceleration of the engine brake. Then, the step proceeds to S42, and driving assistance control is activated. For example, all operable driving assistance controls are activated. Specifically, when the maximum speed suppression control, the erroneous pedal operation reduction control, the front collision warning control, the collision reduction brake control, the collision avoidance control, the lane deviation warning control, the lane deviation suppression control, the evacuation/stopping control, and the follow-up traveling control can be performed as the driving assistance control of the vehicle, all of these controls are activated, and the braking control, the steering control, and the like are executed according to the situation of the vehicle travel. When the vehicle is not traveling on a road exclusive for automobiles, the follow-up traveling control is not activated.

Then, the step proceeds to S44, and it is determined whether there is a cancellation signal of vehicle stop control processing. When it is determined in S44 that there is a cancellation signal of the vehicle stop control processing, the step proceeds to S46, and it is determined whether the cancellation of the vehicle stop control processing is a request of the driver. When it is determined in S46 that the cancellation of the vehicle stop control processing is the request of the driver, the vehicle stop control processing of FIG. 5 is ended. Meanwhile, when it is determined that the cancellation of the vehicle stop control processing is not the request of the driver in S46, the step proceeds to the deceleration control processing of FIG. 6.

When it is determined in S44 that there is no cancellation signal of the vehicle stop control processing, the step proceeds to S48, and it is determined whether the target speed has been reached. That is, it is determined whether the speed of the vehicle has reached the target speed by the deceleration control in S40. When it is determined that the target speed has not been reached in S48, the step returns to S44. Meanwhile, when it is determined that the vehicle speed has reached the target speed in S48, the step proceeds to S50, and a vehicle stop control step is performed.

The vehicle stop control step of S50 is a control for stopping the vehicle. For example, in the vehicle stop control step, first, it is determined whether there is a stop space in the travel path on which the vehicle is traveling. When it is determined that there is a stop space, the vehicle is decelerated toward the stop space, and steering control is also executed as necessary. In this case, a hazard lamp and a brake lamp of the vehicle may be turned on to notify that the vehicle is in the abnormal state after the vehicle is stopped, and treatment of the disease may be performed as necessary.

Meanwhile, in the vehicle stop control step of S50, when it is determined that there is no stop space, the vehicle is caused to travel to a place where the stop space can be detected. In this case, the traveling speed of the vehicle is set to a speed corresponding to the traffic flow. In addition, when the vehicle is traveling on a travel path that cannot be stopped such as a road exclusive for automobiles, the vehicle is caused to travel to a place where the vehicle can be stopped while complying with the speed limit, and the vehicle is caused to stop at the place where the vehicle can be stopped. Then, when the vehicle stop control step of S50 ends, the series of control processing of FIG. 5 ends.

Figure 6:
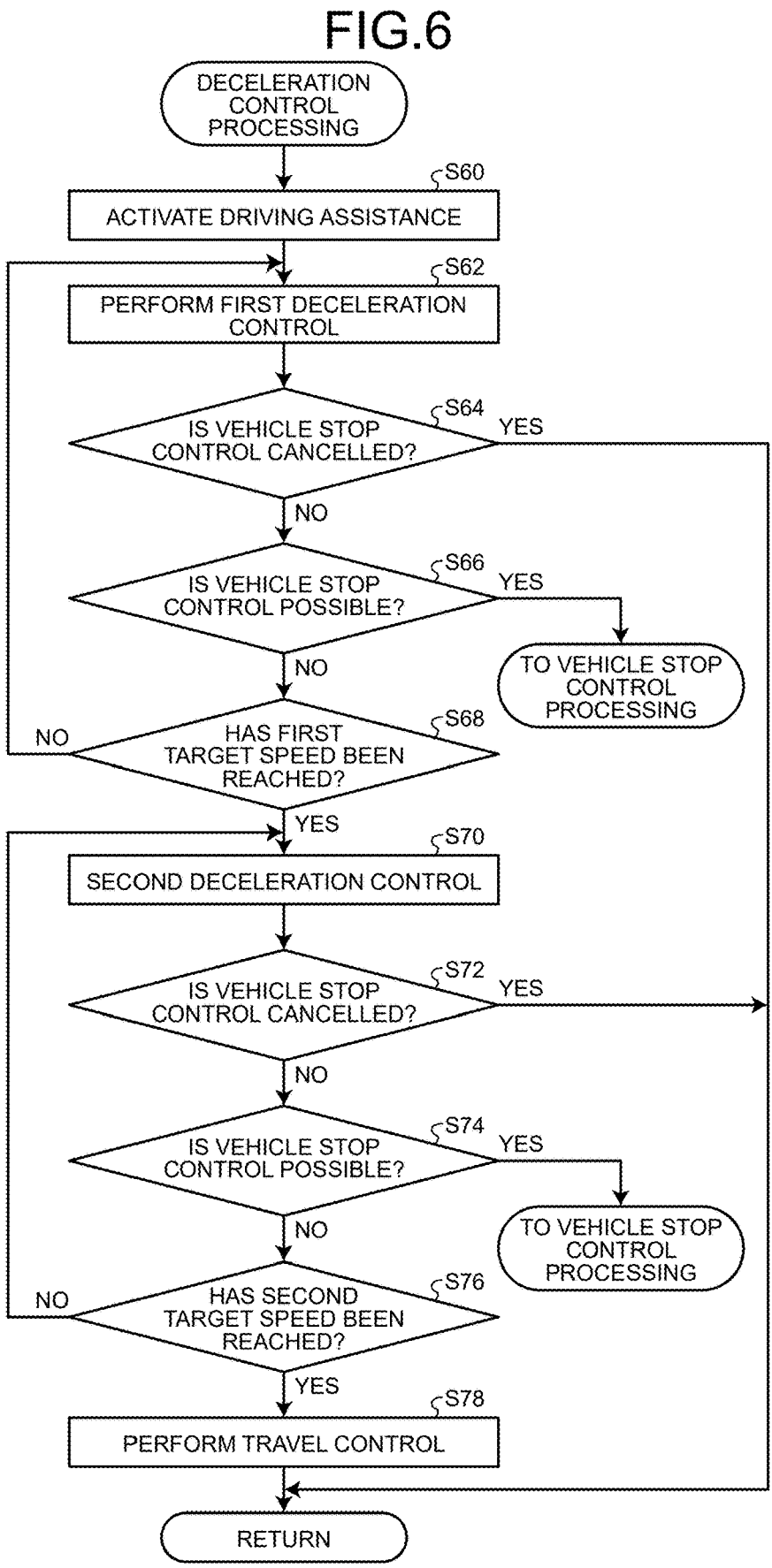
FIG. 6 is a flowchart illustrating the operation of the vehicle control device, the vehicle control method, and deceleration control processing in the vehicle control program according to the embodiment.

FIG. 6 is a flowchart of the deceleration control processing illustrated in S30 of FIG. 4. The control processing of the flowchart of FIG. 6 is executed by the controller 3, for example.

First, as illustrated in S60 of FIG. 6, the driving assistance control is activated. For example, in the driving assistance control of the vehicle, among the maximum speed suppression control, the erroneous pedal operation reduction control, the front collision warning control, the collision reduction brake control, the collision avoidance control, the lane deviation warning control, the lane deviation suppression control, the evacuation/stopping control, and the follow-up traveling control, the maximum speed suppression control, the erroneous pedal operation reduction control, the front collision warning control, and the collision reduction brake control are activated.

Then, as illustrated in S62, a first deceleration control step is performed. The first deceleration control step is a step of decelerating the vehicle by automatic control and setting the speed of the vehicle to the first target speed. For example, in the first deceleration control step, deceleration is performed gently, and the speed is reduced to the first target speed at deceleration of about the deceleration of the engine brake.

Then, the step proceeds to S64, and it is determined whether there is a cancellation signal of the control processing. When it is determined in S64 that there is a cancellation signal of the control processing, the deceleration control processing of FIG. 6 is ended. Meanwhile, when it is determined that the control processing is not cancelled in S64, the step proceeds to S66, and it is determined whether the vehicle stop control processing is possible. Here, when it is determined in S66 that the vehicle stop control processing is possible, the step proceeds to the vehicle stop control processing of FIG. 5.

Meanwhile, when it is determined in S66 that the vehicle stop control processing is not possible, the step proceeds to S68, and it is determined whether the speed of the vehicle has reached the first target speed. When it is determined that the speed of the vehicle has not reached the first target speed in S68, the step returns to the first deceleration control step in S62.

Meanwhile, when it is determined in S68 that the speed of the vehicle has reached the first target speed, the step proceeds to S70, and the second deceleration control step is performed. The second deceleration control step is a step of decelerating the vehicle by automatic control and setting the speed of the vehicle to the second target speed. The second target speed is set to a speed lower than the first target speed. In the second deceleration control step, the speed is gradually reduced to reach the second target speed. In the second deceleration control step, the vehicle exterior notification may be performed, the hazard lamp may be turned on, and the horn may be operated.

Then, the step proceeds to S72, and it is determined whether there is a cancellation signal of the control processing. When it is determined in S72 that there is a cancellation signal of the control processing, the deceleration control processing of FIG. 6 is ended. Meanwhile, when it is determined that the control processing is not cancelled in S72, the step proceeds to S74, and it is determined whether the vehicle stop control processing is possible. Here, when it is determined in S74 that the vehicle stop control processing is possible, the step proceeds to the vehicle stop control processing of FIG. 5.

Meanwhile, when it is determined in S74 that the vehicle stop control processing is not possible, the step proceeds to S76, and it is determined whether the speed of the vehicle has reached the second target speed. When it is determined that the speed of the vehicle has not reached the second target speed in S76, the step returns to the second deceleration control step in S70.

Meanwhile, when it is determined in S76 that the speed of the vehicle has reached the second target speed, the step proceeds to S78, and a travel control step is performed. The travel control step is a control step of causing the vehicle to continuously travel by automatic control. In this case, the vehicle travel is continued except when the driving assistance control in S60 is executed and the vehicle is stopped. In addition, in the travel control step of S76, in a case where monitoring control of the vehicle is possible, the processing of the vehicle control may be performed by remote control. When the traveling control step of S76 ends, the deceleration control processing of FIG. 6 ends.

Figure 7:
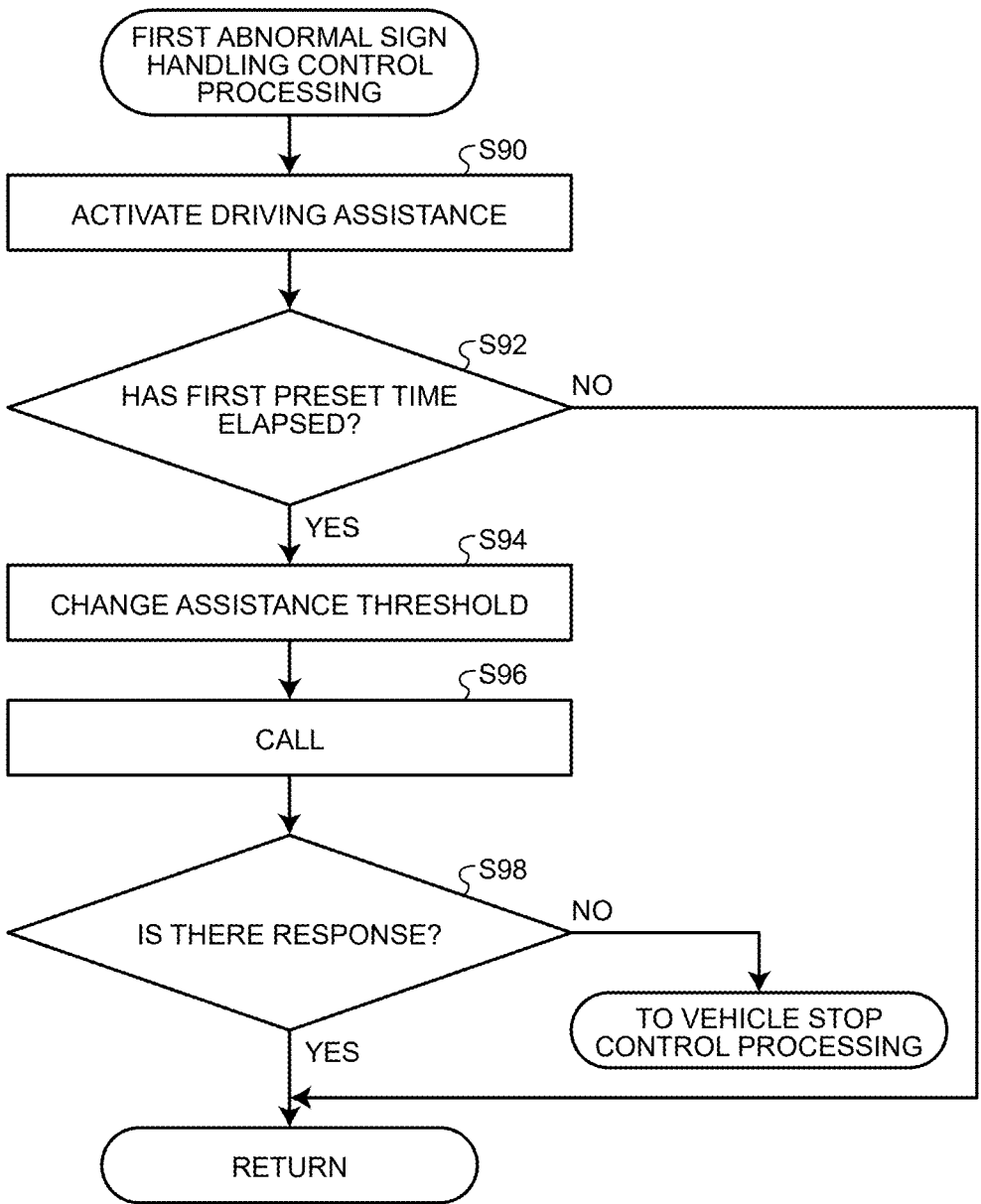
FIG. 7 is a flowchart illustrating the operation of the vehicle control device, the vehicle control method, and first abnormal sign handling control processing in the vehicle control program according to the embodiment.

FIG. 7 is a flowchart of the first abnormal sign handling control processing illustrated in S32 of FIG. 4. The control processing of the flowchart of FIG. 7 is executed by the controller 3, for example.

First, as illustrated in S90 of FIG. 7, the driving assistance control is activated. For example, in the driving assistance control of the vehicle, among the maximum speed suppression control, the erroneous pedal operation reduction control, the front collision warning control, the collision reduction brake control, the collision avoidance control, the lane deviation warning control, the lane deviation suppression control, the lane deviation suppression control, the evacuation/stopping control, and the follow-up traveling control, the maximum speed suppression control, the erroneous pedal operation reduction control, the front collision warning control, the collision reduction brake control, the collision avoidance control, the lane deviation warning control, the lane deviation suppression control, and the evacuation/stopping control are activated. With the activation of the driving assistance control, the vehicle control device 1 can enhance the safety of the vehicle travel when the driver is in the abnormal sign state.

Then, as described in S92, it is determined whether a preset time T4 has elapsed since the time when the abnormal sign state is detected. The time T4 is longer than the time T2, and is set to, for example, about 1.5 minutes. In a case where it is determined in S92 that the time T4 has not elapsed, the first abnormal sign handling control processing of FIG. 7 ends. Meanwhile, when it is determined in S92 that the time T4 has elapsed, the step proceeds to S94, the threshold of execution for the driving assistance control is changed, and the driving assistance control is easily executed. As a result, as the abnormal sign state of the driver continues, the driving assistance control is more likely to be executed, and the safety of the vehicle travel is improved.

Then, the step proceeds to S96, and a call step is performed. The call step is a step of calling to the driver whether the driver can drive the vehicle. For example, the voice may be called by the speaker 52, or the image may be called by the monitor 53.

Then, the step proceeds to S98, and it is determined whether there is a response to the call. For example, it is determined whether there is a response to the call within a preset time T5. The time T5 is set to, for example, about 10 seconds. When there is a response in S98, it is determined that the driver can drive the vehicle, and the first abnormal sign handling control processing in FIG. 7 is ended. Meanwhile, when there is no response in S98, it is determined that the driver is in an incapacity to drive state, and the step proceeds to the vehicle stop control processing of FIG. 5. When S98 ends, the first abnormal sign handling control processing in FIG. 7 ends.

Figure 8:
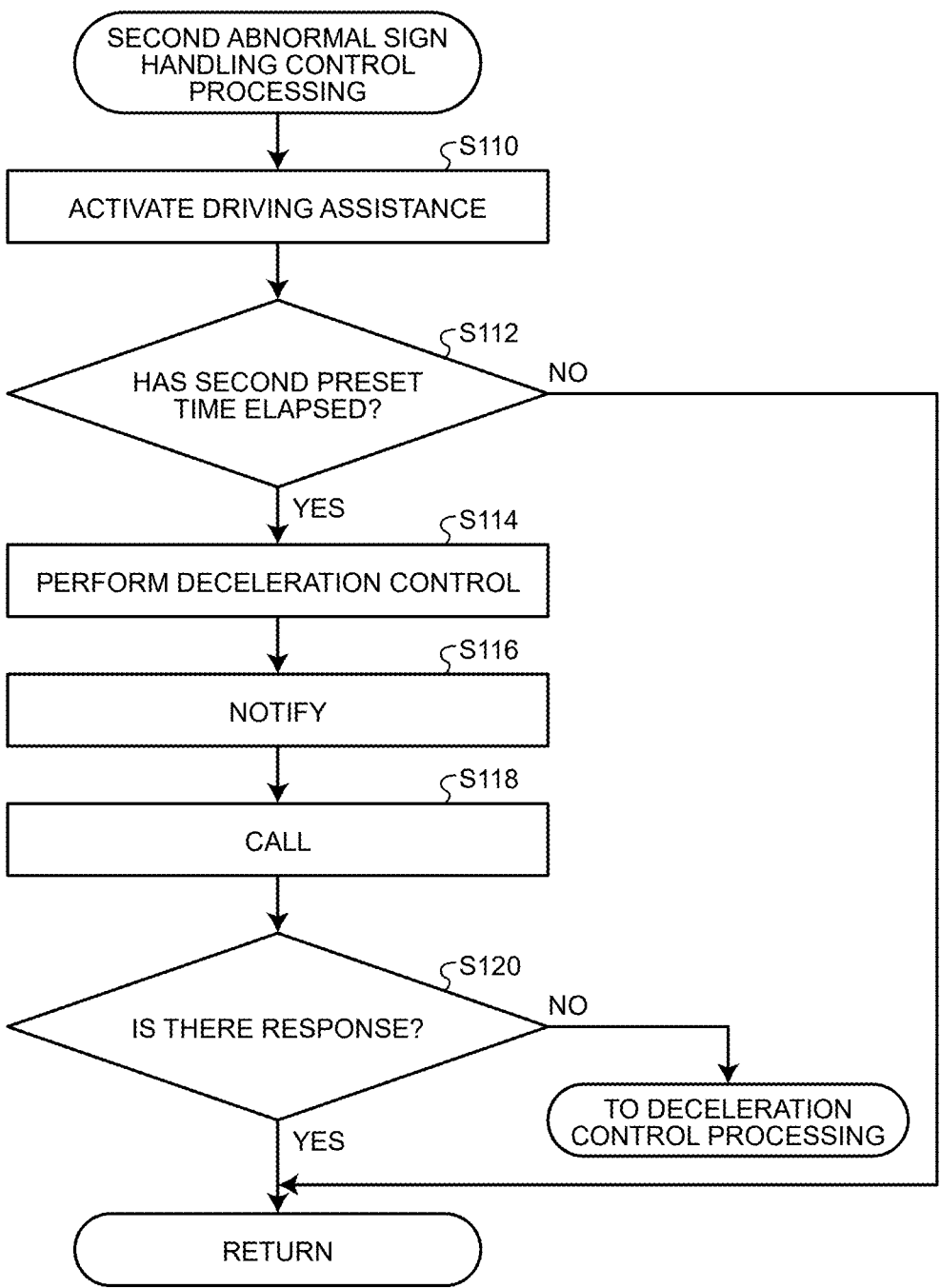
FIG. 8 is a flowchart illustrating the operation of the vehicle control device, the vehicle control method, and second abnormal sign handling control processing in the vehicle control program according to the embodiment.

FIG. 8 is a flowchart of the second abnormal sign handling control processing illustrated in S34 of FIG. 4. The control processing of the flowchart of FIG. 8 is executed by the controller 3, for example.

First, as illustrated in S110 of FIG. 8, the driving assistance control is activated. For example, in the driving assistance control of the vehicle, among the maximum speed suppression control, the erroneous pedal operation reduction control, the front collision warning control, the collision reduction brake control, the collision avoidance control, the lane deviation warning control, the lane deviation suppression control, the evacuation/stopping control, and the follow-up traveling control, the maximum speed suppression control, the erroneous pedal operation reduction control, the front collision warning control, and the collision reduction brake control are activated. With the activation of the driving assistance control, the vehicle control device 1 can enhance the safety of the vehicle travel when the driver is in the abnormal sign state.

Then, as described in S112, it is determined whether a preset time T6 has elapsed since the time when the abnormal sign state is detected. The time T6 is substantially the same as the time T2, and for example, a time of 10 to 60 seconds is set. In a case where it is determined in S112 that the time T6 has not elapsed, the second abnormal sign handling control processing of FIG. 8 is ended. Meanwhile, when it is determined in S112 that the time T6 has elapsed, the step proceeds to S114, and the deceleration control step is performed.

This deceleration control step is a step of decelerating the vehicle by automatic control, and is executed, for example, by gradually decelerating the vehicle until the target speed reaches at deceleration approximately equal to the deceleration of the engine brake.

Then, the step proceeds to S116, and a notification step is performed. In the notification step, the driver is notified that there is an abnormal sign, and is notified that the support by the automatic control cannot be performed due to the restriction in the driving assistance control. This notification is performed, for example, by sound output from the speaker 52 or display output from the monitor 53.

Then, the step proceeds to S118, and the call step is performed. The call step is a step of calling to the driver whether the driver can drive the vehicle. For example, the voice may be called by the speaker 52, or the image may be called by the monitor 53.

Then, the step proceeds to S120, and it is determined whether there is a response to the call of S118. For example, it is determined whether there is a response to the call within a preset time T5. In a case where there is a response in S120, it is determined that the driver can drive the vehicle, and the second abnormal sign handling control processing in FIG. 8 is ended. Meanwhile, when there is no response in S120, the step proceeds to the deceleration control processing of FIG. 6. Upon completion of the step of S120, the second abnormal sign handling control processing of FIG. 8 ends.

As described above, the vehicle control device 1, the vehicle control method, and the vehicle control program according to the present embodiment perform different types of vehicle control according to the situation of the abnormal sign on the driver, so that the driver can perform appropriate vehicle control according to the situation of the abnormal sign, and the safety of the vehicle travel can be secured.

In addition, in the vehicle control device 1, the vehicle control method, and the vehicle control program according to the present embodiment, the vehicle control device 1 according to the present embodiment activates the driving assistance control for enhancing the traveling safety of the vehicle from the time when the driver is determined to be the abnormal sign to the time when the driver is determined to be in the abnormal state, thereby making it possible to ensure the safety of the vehicle travel until the driver is in the abnormal state.

In addition, the vehicle control device 1, the vehicle control method, and the vehicle control program according to the present embodiment can ensure the safety of the vehicle travel by activating at least one of the speed limit control of the vehicle, the erroneous driving operation reduction control, the collision warning control, the collision reduction braking control, the collision avoidance control, the lane deviation warning control, and the lane deviation suppression control as the driving assistance control for enhancing the traveling safety of the vehicle.

In addition, the vehicle control device 1, the vehicle control method, and the vehicle control program according to the present embodiment change the execution threshold of the driving assistance control to make it easier to execute the driving assistance control when a preset time has elapsed since the time when the driver is determined to be the abnormal sign. Therefore, the vehicle control device 1, the vehicle control method, and the vehicle control program according to the present embodiment can enhance the safety of the vehicle travel when the possibility that the driver is in the abnormal state increases.

In addition, the vehicle control device 1, the vehicle control method, and the vehicle control program according to the present embodiment can ensure the safety of the vehicle travel by executing at least the deceleration control of the vehicle when the execution of the driving assistance control is restricted.

Note that the vehicle control device, the vehicle control method, and the vehicle control program according to the present invention are not limited to the above-described embodiments, and various modifications can be made within the scope described in the claims. The vehicle control device 1, the vehicle control method, and the vehicle control program according to the present embodiment may be configured by appropriately combining the components of the embodiment and the modifications described above.

According to the vehicle control device, the vehicle control method, and the vehicle control program according to the present embodiment, it is possible to achieve the safety of the vehicle travel with respect to the abnormality of the driver.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A vehicle control device for autonomously driving a vehicle comprising:

a detection unit that is configured to detect a motion of a driver of the vehicle, a behavior of the vehicle, and biological information of the driver during a manual driving mode of the vehicle in which the driver is operating the vehicle;

an abnormal sign determination unit that is configured to determine whether there is an abnormal sign on the driver during the manual driving mode based on the motion of the driver, the behavior of the vehicle, and the biological information of the driver;

a vehicle controller that is configured to:

transition the vehicle from the manual driving mode to an autonomous driving mode according to a situation of the abnormal sign on the driver; and operate the vehicle in the autonomous driving mode by performing at least a first one of a plurality of driving assistance controls if a travel environment of the vehicle includes a first condition; and a driving assistance determination unit that is configured to restrict from use during the autonomous driving mode at least a second one of the driving assistance controls if the travel environment of the vehicle includes a second condition that is different from the first condition, wherein the driving assistance determination unit is configured to not restrict from use during the autonomous driving mode any of the driving assistance controls if the travel environment of the vehicle includes the first condition.

2. The vehicle control device according to claim 1, wherein the detection unit includes a posture detection unit that is configured to detect a posture in which the driver is in an abnormal state, a motion detection unit that is configured to detect a motion that is the abnormal sign on the driver, a vehicle behavior detection unit that is configured to detect an abnormal behavior of the vehicle associated with the abnormal sign on the driver, and a biological information detection unit that is configured to detect biological information that is the abnormal sign on the driver, the vehicle control device further includes an abnormality determination unit that is configured to determine whether the driver is in the abnormal state by using at least a detection result of the posture detection unit, and the vehicle controller is configured to activate any of the driving assistance controls that are unrestricted from a time when it is determined that the driver has the abnormal sign to a time when it is determined that the driver is in the abnormal state.

3. The vehicle control device according to claim 2, wherein the plurality of driving assistance controls includes at least one of speed limit control of the vehicle, erroneous driving operation reduction control, collision warning control, collision reduction braking control, collision avoidance control, lane deviation warning control, and lane deviation suppression control.

4. The vehicle control device according to claim 3, wherein the vehicle controller is configured to change an execution threshold for the driving assistance controls to make it easier to execute the driving assistance controls when a preset time has elapsed since the time when it is determined that the driver has the abnormal sign.

5. The vehicle control device according to claim 3, wherein when the driving assistance determination unit determines that execution of the at least the second one of the driving assistance controls is restricted, the vehicle controller is configured to execute at least deceleration control of the vehicle.

6. The vehicle control device according to claim 2, wherein the vehicle controller is configured to change an execution threshold for the driving assistance controls to make it easier to execute the driving assistance controls when a preset time has elapsed since the time when it is determined that the driver has the abnormal sign.

7. The vehicle control device according to claim 2, wherein when the driving assistance determination unit determines that execution of the at least second one of the driving assistance controls is restricted, the vehicle controller is configured to execute at least deceleration control of the vehicle.

8. A vehicle control method for autonomously driving a vehicle comprising:

detecting a motion of a driver of the vehicle, a behavior of the vehicle, and biological information of the driver during a manual driving mode of the vehicle in which the driver is operating the vehicle;

determining whether there is an abnormal sign on the driver during the manual driving mode based on the motion of the driver, the behavior of the vehicle, and the biological information of the driver;

transitioning the vehicle from the manual driving mode to an autonomous driving mode according to a situation of the abnormal sign on the driver; and driving the vehicle in the autonomous driving mode by performing at least a first one of a plurality of driving assistance controls if a travel environment of the vehicle includes a first condition;

restricting from use during the autonomous driving mode at least a second one of the driving assistance controls if the travel environment of the vehicle includes a second condition that is different from the first condition; and not restricting from use during the autonomous driving mode any of the driving assistance controls if the travel environment of the vehicle includes the first condition.

9. A non-transitory computer-readable storage medium storing a vehicle control program for causing a computer to execute autonomous driving vehicle control, the vehicle control program comprising:

detecting a motion of a driver of a vehicle, a behavior of the vehicle, and biological information of the driver during a manual driving mode of the vehicle in which the driver is operating the vehicle;

determining whether there is an abnormal sign on the driver during the manual driving mode based on the motion of the driver, the behavior of the vehicle, and the biological information of the driver;

transitioning the vehicle from the manual driving mode to an autonomous driving mode according to a situation of the abnormal sign on the driver;

driving the vehicle in the autonomous driving mode by performing at least a first one of a plurality of driving assistance controls if a travel environment of the vehicle includes a first condition;

restricting from use during the autonomous driving mode at least a second one of the driving assistance controls if the travel environment of the vehicle includes a second condition that is different from the first condition; and not restricting from use during the autonomous driving mode any of the driving assistance controls if the travel environment of the vehicle includes the first condition.

* * * * *